United States Patent
Osawa

(10) Patent No.: US 9,799,818 B2
(45) Date of Patent: Oct. 24, 2017

(54) ULTRASOUND PROBE WITH HEAT COLLECTING PORTION

(71) Applicant: FUJIFILM Corporation, Tokyo (JP)

(72) Inventor: Atsushi Osawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 367 days.

(21) Appl. No.: 14/614,116

(22) Filed: Feb. 4, 2015

(65) Prior Publication Data

US 2015/0270474 A1    Sep. 24, 2015

(30) Foreign Application Priority Data

Mar. 20, 2014  (JP) .................... 2014-058199

(51) Int. Cl.
| | |
|---|---|
| H01L 41/053 | (2006.01) |
| A61B 8/00 | (2006.01) |
| G10K 9/22 | (2006.01) |
| B06B 1/06 | (2006.01) |

(52) U.S. Cl.
CPC .......... *H01L 41/053* (2013.01); *A61B 8/4494* (2013.01); *A61B 8/546* (2013.01); *B06B 1/0644* (2013.01); *G10K 9/22* (2013.01)

(58) Field of Classification Search
CPC ................ A61B 8/00–8/15; H01L 41/053
See application file for complete search history.

(56) References Cited

U.S. PATENT DOCUMENTS

| | | | |
|---|---|---|---|
| 9,419,202 B2 * | 8/2016 | Tai | H01L 41/0825 |
| 2007/0276248 A1 * | 11/2007 | Saito | A61B 8/546 |
| | | | 600/459 |
| 2008/0009742 A1 * | 1/2008 | Kondoh | A61B 8/4281 |
| | | | 600/459 |
| 2008/0077017 A1 * | 3/2008 | Hyuga | A61B 8/12 |
| | | | 600/459 |
| 2009/0062656 A1 * | 3/2009 | Hyuga | A61B 8/12 |
| | | | 600/459 |

(Continued)

FOREIGN PATENT DOCUMENTS

| | | | |
|---|---|---|---|
| EP | 0727259 A2 * | 8/1996 | ........... B06B 1/0681 |
| JP | 2-91510 U | 7/1990 | |

(Continued)

OTHER PUBLICATIONS

Japanese Office Action dated Mar. 1, 2016, for Japanese Application No. 2014-058199 with the English translation.

*Primary Examiner* — J. San Martin
(74) *Attorney, Agent, or Firm* — Birch, Stewart, Kolasch & Birch, LLP

(57) ABSTRACT

There is provided an ultrasound probe capable of efficiently discharging heat generated in a plurality of piezoelectric elements to the outside. A heat collecting portion that includes at least one heat conducting path and is formed of a material having a higher thermal conductivity than a backing member collects heat from a plurality of piezoelectric elements, and a heat exhausting portion connected to the heat collecting portion discharges the heat collected in the heat collecting portion to the outside. The heat conducting path extends in a thickness direction within the backing member and has a distal end exposed from the top surface of the backing member facing the bottom surface of each of the plurality of piezoelectric elements.

18 Claims, 6 Drawing Sheets

(56) References Cited

U.S. PATENT DOCUMENTS

| | | | |
|---|---|---|---|
| 2010/0125209 A1* | 5/2010 | Lee | B06B 1/0629 |
| | | | 600/459 |
| 2011/0114303 A1* | 5/2011 | Rhim | A61B 8/00 |
| | | | 165/185 |
| 2015/0157292 A1* | 6/2015 | Gu | A61B 8/4444 |
| | | | 600/459 |

FOREIGN PATENT DOCUMENTS

| | | |
|---|---|---|
| JP | 10-94540 A | 4/1998 |
| JP | 2005-103078 A | 4/2005 |
| JP | 2005-347804 A | 12/2005 |
| JP | 2007-282743 A | 11/2007 |
| KR | WO 2016117721 A1 * 7/2016 | ............... A61B 8/00 |

* cited by examiner

ULTRASOUND PROBE WITH HEAT COLLECTING PORTION

CROSS-REFERENCE TO RELATED APPLICATIONS

The present application claims priority under 35 U.S.C. §119 to Japanese Patent Application No. 2014-058199, filed on Mar. 20, 2014. The above application is hereby expressly incorporated by reference, in its entirety, into the present application.

BACKGROUND OF THE INVENTION

1. Field of the Invention

The present invention relates to an ultrasound probe, and in particular, an ultrasound probe including a heat collecting portion for collecting heat from a plurality of piezoelectric elements.

2. Description of the Related Art

In the medical field, an ultrasound diagnostic apparatus using an ultrasound image has been put into practical use. In general, this kind of ultrasound diagnostic apparatus generates an ultrasound image by transmitting an ultrasonic beam toward a subject from an ultrasound probe, receiving an ultrasonic echo from the subject, and processing the received signal electrically.

In recent years, a voltage applied to a plurality of piezoelectric elements built in the ultrasound probe and power consumption have increased with the advancement of the ultrasound diagnostic apparatus, and heat generation of the plurality of piezoelectric elements has become a problem. When a plurality of piezoelectric elements generate heat, the heat generated in the plurality of piezoelectric elements is conducted to an acoustic lens through an acoustic matching layer disposed above the piezoelectric elements or the like since the thermal conductivity of a backing member disposed below the piezoelectric elements is low. As a result, the surface temperature of the acoustic lens is increased.

The acoustic lens is located at the distal end of the ultrasound probe and is in direct contact with the human body. For this reason, the surface temperature needs to be suppressed so as not to exceed the upper limit defined, for example, in ISO60601-2-37 from the point of view of safety. Therefore, the driving of a plurality of piezoelectric elements is limited so that the surface of the acoustic lens does not have a high temperature. Specifically, the driving conditions of a plurality of piezoelectric elements, for example, a voltage, a wave number, a driving frequency, and a repetition frequency are limited, and transmission and reception sound pressure is limited. Due to the limitation on the driving conditions of a plurality of piezoelectric elements, the S/N ratio of the ultrasound image obtained by transmitting and receiving ultrasonic waves has been suppressed.

As an ultrasound probe for suppressing the temperature rise of a plurality of piezoelectric elements, for example, an ultrasound probe in which a first backing member as a high attenuation medium is provided immediately below each piezoelectric element and a second backing member as a heat conductor having a high heat conductivity is provided immediately below the groove disposed between the piezoelectric elements has been proposed in JP2007-282743A. Thus, it is possible to suppress the temperature rise of the piezoelectric elements by decelerating the ultrasonic wave using the first backing member while discharging the heat generated in a plurality of piezoelectric elements to the outside using the second backing member.

SUMMARY OF THE INVENTION

However, the second backing member that is a heat conductor having a high heat conductivity is not exposed from the top surface of the first backing member bonded to the bottom surfaces of a plurality of piezoelectric elements. That is, the second backing member is disposed inside the first backing member (below the top surface of the first backing member). For this reason, a sufficient amount of heat could not be conducted to the second backing member from the plurality of piezoelectric elements.

The invention has been made to solve the aforementioned problems in the related art, and it is an object of the invention to provide an ultrasound probe capable of efficiently discharging the heat generated in a plurality of piezoelectric elements to the outside. According to an aspect of the invention, there is provided an ultrasound probe including: a backing member; a plurality of piezoelectric elements arrayed on a top surface of the backing member; a heat collecting portion that includes at least one heat conducting path, is formed of a material having a higher thermal conductivity than the backing member, and collects heat from the plurality of piezoelectric elements, the heat conducting path extending in a thickness direction within the backing member and having a distal end exposed from the top surface of the backing member facing a bottom surface of each of the plurality of piezoelectric elements; and a heat exhausting portion that is connected to the heat collecting portion and discharges heat collected in the heat collecting portion to an outside. Here, the "bottom surface of the piezoelectric element" refers to a surface on a side where the piezoelectric element is in contact with the backing member.

The heat conducting path may be disposed immediately below at least one of a pair of edge portions extending in an azimuth direction on the bottom surface of each of the plurality of piezoelectric elements, and the distal end may be in direct contact with at least one of the pair of edge portions of each of the plurality of piezoelectric elements.

The heat conducting path may be disposed immediately below an intermediate portion located between the pair of edge portions on the bottom surface of each of the plurality of piezoelectric elements, and the distal end may be in direct contact with the intermediate portion of each of the plurality of piezoelectric elements.

The ultrasound probe may further include a plurality of separating portions that are filled between the plurality of piezoelectric elements in order to separate the plurality of piezoelectric elements from each other and that are formed of a material having a higher thermal conductivity than the backing member. The heat conducting path may be disposed immediately below the plurality of separating portions, and the distal end is in direct contact with the plurality of separating portions.

The ultrasound probe may further include a de-matching layer disposed between the backing member and the plurality of piezoelectric elements. The heat conducting path may extend from an inside of the backing member to an inside of the de-matching layer. The distal end may be exposed from a top surface of the de-matching layer.

The heat conducting path may have a shape having a cross-sectional area that decreases toward the distal end.

The heat collecting portion may include a heat collecting plate connected to a base end of the heat conducting path.

The heat collecting plate may be disposed inside the backing member and may have a plurality of inclined surfaces on a surface facing the plurality of piezoelectric elements, the inclined surfaces being inclined with respect to the bottom surfaces of the plurality of piezoelectric elements.

The heat collecting plate may be disposed inside the backing member and may include cavities, and the cavities may have a plurality of inclined surfaces that are inclined with respect to the bottom surfaces of the plurality of piezoelectric elements.

The heat exhausting portion may be a heat pipe having a distal end connected to the heat collecting portion.

According to the invention, the heat collecting portion including a plurality of heat conducting paths having distal ends exposed from the top surface of the backing member facing the bottom surfaces of the plurality of piezoelectric elements collects heat from the plurality of piezoelectric elements, and the heat exhausting portion connected to the heat collecting portion discharges the heat collected in the heat collecting portion to the outside. Therefore, it is possible to efficiently discharge the heat generated in the plurality of piezoelectric elements to the outside.

DESCRIPTION OF THE PREFERRED EMBODIMENTS

Hereinafter, embodiments of the invention will be described with reference to the accompanying diagrams.

First Embodiment

Figure 1:
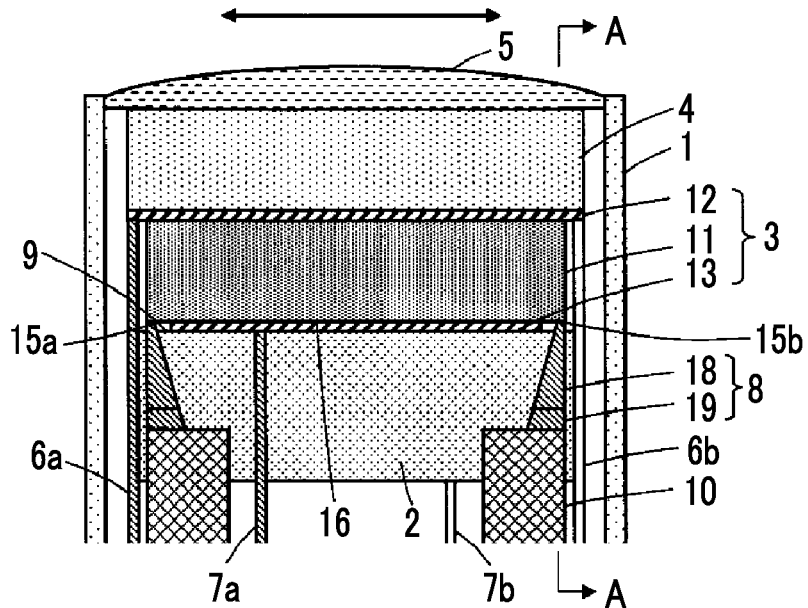
FIG. 1 is a cross-sectional view showing the configuration of an ultrasound probe according to a first embodiment of the invention.

FIG. 1 shows the configuration of an ultrasound probe according to a first embodiment of the invention. An ultrasound probe includes a housing 1. In the housing 1, a backing member 2, a plurality of piezoelectric elements 3, an acoustic matching layer 4, and an acoustic lens 5 are sequentially laminated and disposed. The acoustic lens 5 is exposed to the outside from the distal end of the housing 1, and the outer edge of the acoustic lens 5 is fixed to the distal end of the housing 1.

Ground lines 6a and 6b and signal lines 7a and 7b are connected to the plurality of piezoelectric elements 3. In addition, the ultrasound probe includes a heat collecting portion 8 disposed inside the backing member 2 and a heat exhausting portion 10 connected to the heat collecting portion 8. The heat collecting portion 8 connects the bottom surfaces of the plurality of piezoelectric elements 3 to the heat exhausting portion 10.

The housing 1 forms the outer surface of the ultrasound probe, and is gripped by the operator in the ultrasound diagnosis.

The backing member 2 is provided to absorb ultrasonic waves emitted rearward from the plurality of piezoelectric elements 3, and is formed of natural rubber, chlorinated polyethylene, urethane rubber, or epoxy resin, for example. The backing member 2 having a thermal conductivity of, for example, 0.1 W/mK to 1.0 W/mK is used.

Figure 2:
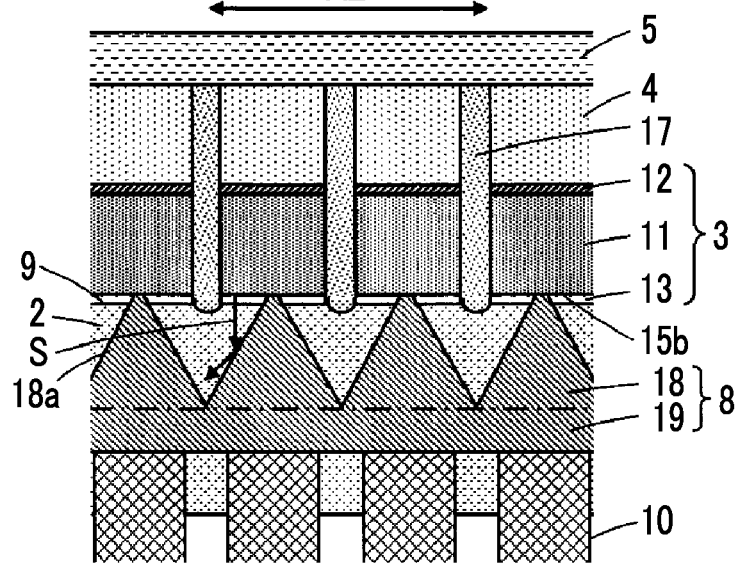
FIG. 2 is a cross-sectional view taken along the line A-A of FIG. 1.

FIG. 2 shows a cross-sectional view taken along the line A-A of FIG. 1.

As shown in FIG. 2, the plurality of piezoelectric elements 3 are arrayed in a row at equal pitches on a top surface 9 of the backing member 2. The plurality of piezoelectric elements 3 have a plurality of piezoelectric bodies 11 that are separated from each other. It is possible to bond a ground electrode layer 12 to the top surface of each piezoelectric body 11 and to bond a signal electrode layer 13 to the bottom surface of each piezoelectric body 11.

Here, it is assumed that the arrangement direction of the plurality of piezoelectric elements 3 is an azimuth direction AZ and a direction, which is parallel to the bottom surfaces of the plurality of piezoelectric elements and is perpendicular to the azimuth direction AZ is an elevation direction EL.

Figure 3:
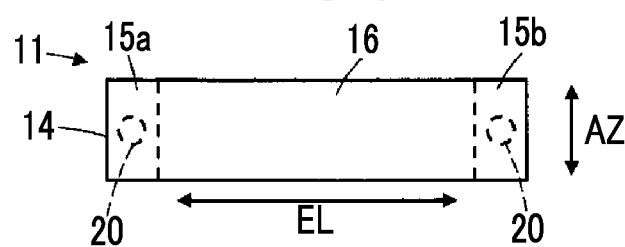
FIG. 3 is a diagram showing the bottom surface of a piezoelectric body.

FIG. 3 shows a bottom surface 14 of the piezoelectric body 11. As shown in FIG. 3, each of the plurality of piezoelectric bodies 11 includes a pair of edge portions 15a and 15b extending in the azimuth direction AZ on the bottom surface 14 and an intermediate portion 16 located between the pair of edge portions 15a and 15b. The intermediate portion 16 is a portion of the piezoelectric body 11 that expands and contracts greatly, and the pair of edge portions 15a and 15b are portions of the piezoelectric body 11 that expand and contract very little compared with the intermediate portion 16.

Each of the pair of edge portions 15a and 15b includes a contact portion 20 in contact with the distal end of the heat collecting portion 8, that is, the distal end of a heat conducting path 18 to be described later. Thus, since the pair of edge portions 15a and 15b of the piezoelectric body 11 that expand and contract little are in direct contact with the distal end of the heat collecting portion 8, it is possible to suppress the influence of distortion or the like on the received signal.

Specifically, each of the pair of edge portions 15a and 15b is provided in a length range of 1/10 or less of the width of the piezoelectric body 11 extending in the elevation direction EL. Accordingly, it is possible to suppress the influence of echo ringing or band characteristics of the oscillator due to the contact of the heat collecting portion 8. For example, in the case of a piezoelectric body having a width of 5.0 mm, if the range of about 0.5 mm is assumed for each of the pair of edge portions 15a and 15b, the above-described influence is small.

The ground electrode layer 12 can be formed to be longer than the width of the piezoelectric body 11, which extends in the elevation direction EL, so as to cover the entire top surface of the piezoelectric body 11, and can be disposed such that a pair of opposite edge portions protrude from the top surface of the piezoelectric body 11 in the elevation direction EL.

The signal electrode layer 13 has the same surface area as the intermediate portion 16 of the piezoelectric body 11, and is disposed so as to cover the entire surface of the intermediate portion 16. Accordingly, the pair of edge portions 15a and 15b of the piezoelectric body 11 is exposed.

Preferably, the plurality of piezoelectric bodies 11 are formed of Pb-based perovskite structure oxide. For example, the plurality of piezoelectric bodies 11 can be formed of Pb-based piezoelectric ceramic represented by lead zirconate titanate (Pb(Zr, Ti)O$_3$) or relaxor-based piezoelectric single crystal represented by magnesium niobate-lead titanate solid solution (PMN-PT) and zinc niobate-lead titanate solid solution (PZN-PT). In addition, the plurality of piezoelectric bodies 11 can also be formed of vinylidene fluoride (VDF) based materials.

The acoustic matching layer 4 is provided to make an ultrasonic beam transmitted from the plurality of piezoelectric elements 3 incident on the inside of the subject efficiently, and is formed of a material having an acoustic impedance of the intermediate value between the acoustic impedance of each piezoelectric element 3 and the acoustic impedance of the living body. The acoustic matching layer 4 is divided into a plurality of pieces, and the plurality of pieces can be bonded onto the top surfaces of the plurality of piezoelectric elements 3 so as to correspond to each other. That is, the acoustic matching layer 4 can be arrayed in a row in the azimuth direction AZ at the same pitch as the plurality of piezoelectric elements 3.

A separating portion 17 that separates the plurality of piezoelectric elements 3 from each other and separates a plurality of pieces of the acoustic matching layer 4 from each other is disposed between the plurality of piezoelectric elements 3 and between the plurality of pieces of the acoustic matching layer 4. That is, the separating portions 17 are disposed so as to be parallel to each other in the lamination direction in a range from the surface of the plurality of piezoelectric elements 3 to the surface of the backing member 2. The separating portion 17 is provided to fix the positions of the plurality of piezoelectric elements 3 and adjacent pieces in the acoustic matching layer 4, and can be formed of epoxy resin, for example. By filling such a material between the plurality of piezoelectric elements 3 and between the plurality of pieces of the acoustic matching layer 4, the separating portion 17 can be formed.

The acoustic lens 5 is provided to extract an ultrasonic beam using refraction and improve the resolution in the elevation direction, and is formed of silicone rubber or the like.

The heat collecting portion 8 is formed of a material having a higher thermal conductivity than the backing member 2, and collects the heat generated in the plurality of piezoelectric elements 3. The heat collecting portion 8 includes a plurality of heat conducting paths 18, which extend in the thickness direction within the backing member 2 and which have distal ends exposed from the top surface 9 of the backing member 2 facing the bottom surface 14 of the plurality of piezoelectric elements 3, and a heat collecting plate 19 connected to base ends of the plurality of heat conducting paths 18.

Preferably, the heat collecting portion 8 has a higher thermal conductivity than the acoustic matching layer 4. Specifically, it is preferable that the heat collecting portion 8 have a thermal conductivity of 200 W/mK to 500 W/mK. For example, the heat collecting portion 8 can be formed of a metal, such as copper, aluminum, and gold.

The plurality of heat conducting paths 18 are provided to conduct the heat generated in the plurality of piezoelectric elements 3 to the base end side. As shown in FIG. 1, the plurality of heat conducting paths 18 are disposed immediately below the edge portions 15a and 15b of the plurality of piezoelectric bodies 11. In addition, as shown in FIG. 2, the plurality of heat conducting paths 18 are arrayed in the azimuth direction AZ so as to correspond to the respective piezoelectric elements 3. That is, the plurality of heat conducting paths 18 are arrayed in a row in the azimuth direction AZ immediately below the edge portions 15a and 15b of the plurality of piezoelectric bodies 11.

In addition, each of the plurality of heat conducting paths 18 has a shape having a cross-sectional area that decreases continuously toward the distal end, and the heat conducting paths 18 adjacent to each other in the azimuth direction AZ are connect to each other near the base ends. Accordingly, the entire surface of the heat collecting portion 8 facing the bottom surfaces 14 of the plurality of piezoelectric elements 3 can be formed as an inclined surface 18a that is inclined with respect to the bottom surface 14. In addition, the distal ends of the plurality of heat conducting paths 18 protrude from the top surface 9 of the backing member 2 and extend along the horizontal side of the signal electrode layer 13, and are in direct contact with the contact portions 20 of the pair of edge portions 15a and 15b on the bottom surfaces 14 of the plurality of piezoelectric bodies 11 shown in FIG. 3.

The heat collecting plate 19 is provided to collect the heat conducted from each heat conducting path 18. The heat collecting plate 19 is disposed at a position where ultrasonic waves emitted rearward from the plurality of piezoelectric elements 3 are sufficiently attenuated, within the backing member 2, so as to be parallel to the bottom surfaces 14 of the plurality of piezoelectric elements 3. For example, the heat collecting plate 19 can be disposed at a position distant from the bottom surfaces of the plurality of piezoelectric elements 3 by 1.0 mm or more. In addition, the plurality of heat conducting paths 18 are connected to the heat collecting plate 19 so as to cover the entire top surface.

The heat exhausting portion 10 is formed by a plurality of heat pipes having distal ends connected to the heat collecting plate 19, and is provided to discharge the heat collected in the heat collecting plate 19 to the outside. As shown in FIG. 2, it is preferable that the heat exhausting portion 10 be disposed so as to correspond to the plurality of heat conducting paths 18 in a one-to-one manner.

The signal lines 7a and 7b are disposed so as to pass between the heat conducting paths 18 disposed immediately below the pair of edge portions 15a and 15b of the plurality of piezoelectric elements 3, and are alternately connected to the signal electrode layers 13 of the plurality of piezoelectric elements 3 arrayed in the azimuth direction AZ. For example, the signal line 7a can be connected to the signal electrode layer 13 of the piezoelectric element 3 arrayed at an even-numbered position in the azimuth direction AZ, and the signal line 7b can be connected to the signal electrode layer 13 of the piezoelectric element 3 arrayed at an odd-numbered position.

The ground lines 6a and 6b are disposed on the sides of both edge portions protruding in the elevation direction EL in the ground electrode layer 12, and can be alternately connected to the ground electrode layers 12 of the plurality of piezoelectric elements 3 arrayed in the azimuth direction AZ in the same manner as the signal lines 7a and 7b.

Next, the operation of the present embodiment will be described.

First, the acoustic lens 5 of the ultrasound probe shown in FIG. 1 is brought into contact with a subject to apply a pulsed or continuous-wave voltage between the signal electrode layer 13 and the ground electrode layer 12 of the plurality of piezoelectric elements 3 through the signal lines 7a and 7b and the ground lines 6a and 6b. Then, the piezoelectric body 11 of each piezoelectric element 3 expands and contracts to generate pulsed or continuous-wave ultrasonic waves, and the ultrasonic waves are transmitted into the subject through the acoustic matching layer 4 and the acoustic lens 5.

In this case, an ultrasonic wave S is also emitted to the rear side of the plurality of piezoelectric elements 3, but the ultrasonic wave S is absorbed by the backing member 2. Since the plurality of heat conducting paths 18 disposed inside the backing member 2 are disposed immediately below the pair of edge portions 15a and 15b, which expand and contract very little, in the piezoelectric body 11, the absorption of the ultrasonic wave S by the backing member 2 is not significantly inhibited.

In addition, each of the plurality of heat conducting paths 18 is formed such that the cross-sectional area is continuously decreased toward the distal end, and has the inclined surface 18a, which is inclined with respect to the bottom surfaces 14 of the plurality of piezoelectric elements 3, as its top surface. Therefore, as shown in FIG. 2, even if the ultrasonic wave S emitted to the rear side of the plurality of piezoelectric elements 3 is incident on the plurality of heat conducting paths 18, the ultrasonic wave S can be scattered downward by the inclined surface 18a. As a result, it is possible to suppress a situation where the ultrasonic wave S reflected by the plurality of heat conducting paths 18 is incident on the bottom surfaces of the plurality of piezoelectric elements 3.

In addition, when generating an ultrasonic wave, heat is generated in the plurality of piezoelectric elements 3 due to the expansion and contraction of the piezoelectric body 11. The pair of edge portions 15a and 15b on the bottom surface 14 of the piezoelectric body 11 is in direct contact with the distal ends of the plurality of heat conducting paths 18. Accordingly, heat generated in the piezoelectric body 11 through the distal ends of the plurality of heat conducting paths 18 can be sequentially transferred to the plurality of heat conducting paths 18. Then, the heat transferred to the plurality of heat conducting paths 18 is conducted to the base ends of the heat conducting paths 18, thereby being transferred to the heat collecting plate 19. In this manner, the heat generated in the plurality of piezoelectric elements 3 can be collected in the heat collecting portion 8.

The heat collected in the heat collecting portion 8 is discharged to the outside through the heat exhausting portion 10 connected to the heat collecting plate 19. Since the heat exhausting portion 10 is formed by heat pipes and has a thermal conductivity of, for example, 1000 W/mK to 10000 W/mK, the heat collected in the heat collecting portion 8 can be efficiently discharged to the outside.

Thus, since the heat from the plurality of piezoelectric elements 3 is collected by the heat collecting portion 8 and the heat collected in the heat collecting portion 8 is sequentially discharged to the outside by the heat exhausting portion 10, the heat generated in the plurality of piezoelectric elements 3 can be efficiently discharged to the outside. Therefore, it is possible to suppress a situation where the heat from the plurality of piezoelectric elements 3 is conducted to the acoustic lens 5 to increase the surface temperature of the acoustic lens 5.

Subsequently, the ultrasonic wave transmitted toward the subject from the ultrasound probe is reflected within the subject and is then incident on each piezoelectric element 3 through the acoustic lens 5 and the acoustic matching layer 4 of the ultrasound probe. In response to the ultrasonic wave incident on each piezoelectric element 3, the piezoelectric body 11 expands and contracts to generate an electrical signal between the signal electrode layer 13 and the ground electrode layer 12, and the electrical signal is output as a received signal through the signal lines 7a and 7b.

In this case, the distal ends of the plurality of heat conducting paths 18 are in contact with the pair of edge portions 15a and 15b of the piezoelectric body 11, which expand and contract very little, on the bottom surface 14 of the piezoelectric body 11. Therefore, since the expansion and contraction of the piezoelectric body 11 due to the reception of the ultrasonic wave are not significantly inhibited, it is possible to suppress the occurrence of distortion or the like in the received signal due to the arrangement of the plurality of heat conducting paths 18.

According to the present embodiment, since the heat generated in the plurality of piezoelectric elements 3 is efficiently discharged to the outside, it is possible to maintain the low surface temperature of the acoustic lens 5 even if the driving force of the plurality of piezoelectric elements is increased. Therefore, it is possible to improve the S/N ratio of the ultrasound image by increasing the driving force of the plurality of piezoelectric elements. In addition, the plurality of heat conducting paths 18 are disposed at positions where the expansion and contraction of the plurality of piezoelectric bodies 11 are not inhibited, and each heat conducting path 18 has a shape for scattering the ultrasonic wave S that is emitted rearward from the plurality of piezoelectric elements 3. Therefore, it is possible to efficiently discharge the heat from the plurality of piezoelectric elements 3 while suppressing the influence on the received signal due to the arrangement of the plurality of heat conducting paths 18.

Second Embodiment

The heat collecting portion and the heat exhausting portion of the invention can be applied to any ultrasound probe configured to include a backing member and a plurality of piezoelectric elements arrayed on the surface of the backing member, and are not particularly limited.

Figure 4:
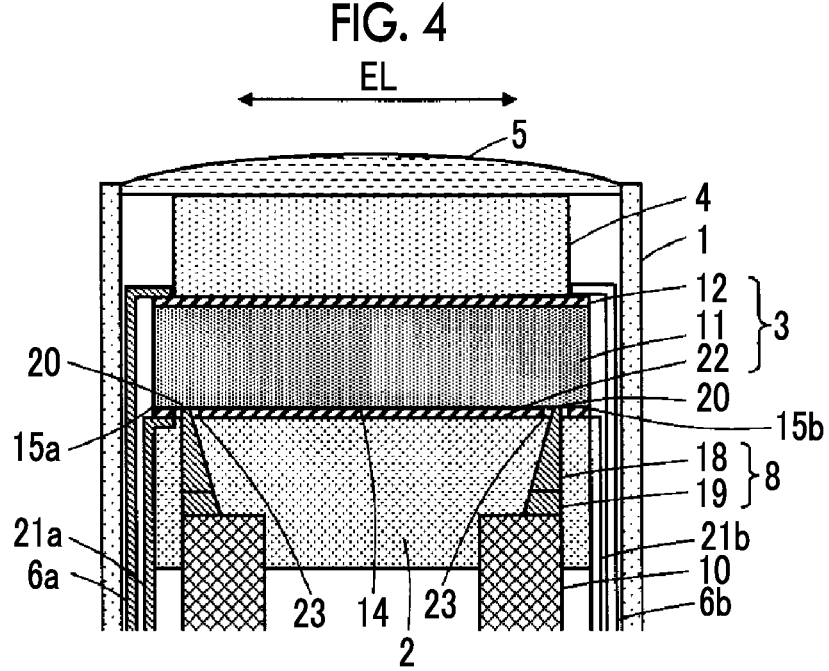
FIG. 4 is a cross-sectional view showing the configuration of an ultrasound probe according to a second embodiment.

For example, although the signal lines 7a and 7b are connected to the intermediate portion 16 of the signal electrode layer 13 so as to pass through the heat conducting path 18 in the first embodiment, signal lines 21a and 21b can also be disposed so as to pass along the outside of the heat conducting path 18 as shown in FIG. 4.

Specifically, in the ultrasound probe according to the first embodiment, a signal electrode layer 22 that covers the entire bottom surface 14 of the piezoelectric body 11 can be disposed instead of the signal electrode layer 13 and the signal lines 7a and 7b, and the signal lines 21a and 21b can be connected at positions corresponding to the pair of edge portions 15a and 15b of the piezoelectric body 11 on the bottom surface of the signal electrode layer 22. In the signal electrode layer 22, an opening 23 is formed at a position corresponding to the contact portion 20 in the pair of edge portions 15a and 15b. Therefore, the distal ends of the plurality of heat conducting paths 18 can be brought into direct contact with the bottom surface 14 of the piezoelectric body 11 through the opening 23.

According to the present embodiment, since the heat generated in the plurality of piezoelectric elements 3 is efficiently discharged to the outside, it is possible to maintain the low surface temperature of the acoustic lens 5 even if the driving force of the plurality of piezoelectric elements is increased. Therefore, it is possible to improve the S/N ratio of the ultrasound image by increasing the driving force of the plurality of piezoelectric elements. In addition, the plurality of heat conducting paths 18 are disposed at positions where the expansion and contraction of the plurality of piezoelectric bodies 11 are not inhibited, and each heat conducting path 18 has a shape for scattering the ultrasonic wave S that is emitted rearward from the plurality of piezoelectric elements 3. Therefore, it is possible to efficiently discharge the heat from the plurality of piezoelectric elements 3 while suppressing the influence on the received signal due to the arrangement of the plurality of heat conducting paths 18.

On the other hand, in the ultrasound probe according to the first embodiment, the signal lines 7a and 7b are not connected to the pair of edge portions 15a and 15b of the signal electrode layer 13. Accordingly, since the contact portion 20 that is in contact with the plurality of heat conducting paths 18 can be widened to the pair of edge portions 15a and 15b of the piezoelectric body 11, it is possible to easily align the plurality of heat conducting paths 18 and the contact portion 20. In addition, since the plurality of heat conducting paths 18 can be disposed more outward, it is possible to dispose the plurality of heat conducting paths 18 so as not to further inhibit the expansion and contraction of the piezoelectric body 11.

Third Embodiment

Although the distal ends of the plurality of heat conducting paths 18 are in direct contact with the pair of edge portions 15a and 15b of the plurality of piezoelectric elements 3 in the first and second embodiments, the distal ends of the plurality of heat conducting paths 18 may be exposed from the surface of the backing member 2 so that the heat from the plurality of piezoelectric elements 3 can be efficiently collected, and the invention is not limited to this.

Figure 5:
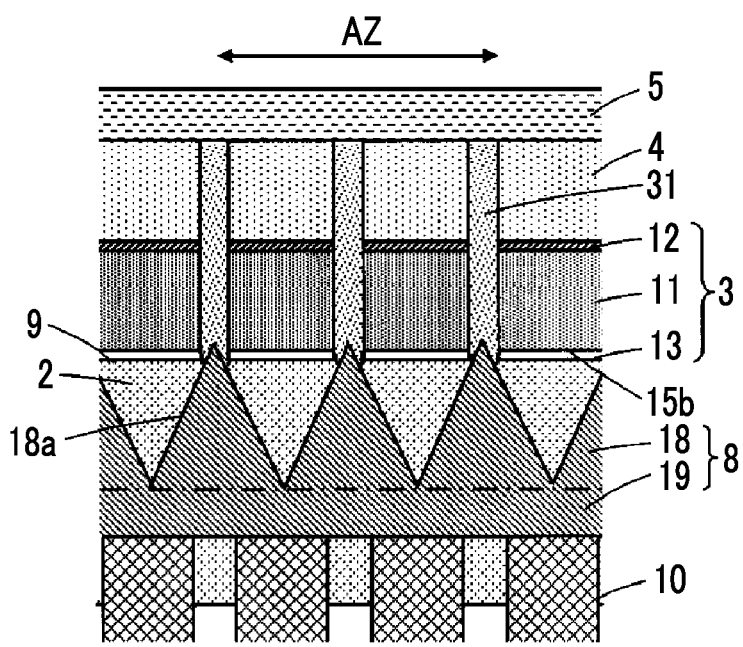
FIG. 5 is a cross-sectional view showing the configuration of an ultrasound probe according to a third embodiment.

For example, in the ultrasound probe shown in the first embodiment, as shown in FIG. 5, a plurality of separating portions 31 that are filled between the plurality of piezoelectric elements 3 in order to separate the plurality of piezoelectric elements 3 from each other may be formed of a material having a higher thermal conductivity than the backing member 2, and the plurality of heat conducting paths 18 may be disposed immediately below the plurality of separating portions 31 and the distal ends may be inserted into the separating portions 31 so that the distal ends of the plurality of heat conducting paths 18 are in direct contact with the plurality of separating portions 31.

Heat generated in the plurality of piezoelectric elements 3 is sequentially conducted to the distal ends of the plurality of heat conducting paths 18 through the plurality of separating portions 31, and is then conducted toward the base ends from the distal ends of the plurality of heat conducting paths 18. Then, the heat conducted to the base ends of the plurality of heat conducting paths 18 can be discharged to the outside through the heat collecting plate 19 and the heat exhausting portion 10.

According to the present embodiment, since the plurality of heat conducting paths 18 are not in direct contact with the plurality of piezoelectric bodies 11, it is possible to reliably suppress the influence on the received signal due to the arrangement of the plurality of heat conducting paths 18 without interfering with the expansion and contraction of the piezoelectric body 11.

In addition, the plurality of separating portions 31 can be formed of a material obtained by mixing a resin material with particles of boron nitride, for example. Preferably, each of the plurality of separating portions 31 has a thermal conductivity of 1.0 W/mK to 5.0 W/mK.

Fourth Embodiment

Although the heat collecting plate 19 is disposed only below the plurality of heat conducting paths 18 and the entire top surface of the heat collecting plate 19 is covered by the plurality of heat conducting paths 18 in the first to third embodiments described above, the heat collecting plate 19 can also be formed such that the top surface is exposed. In this case, it is preferable to form a plurality of inclined surfaces, which are inclined with respect to the bottom surfaces 14 of the plurality of piezoelectric elements 3, on the top surface through which the heat collecting plate 19 is exposed.

Figure 6:
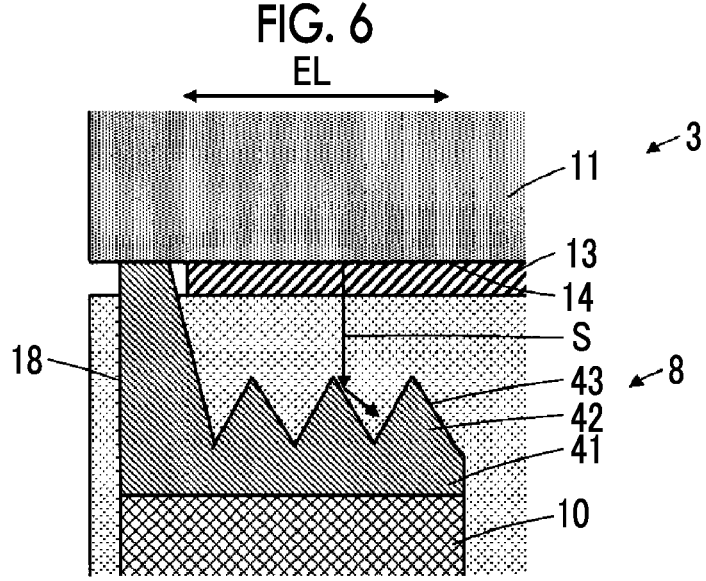
FIG. 6 is a cross-sectional view showing the configuration of an ultrasound probe according to a fourth embodiment.

For example, in the ultrasound probe according to the first embodiment, as shown in FIG. 6, it is possible to dispose a heat collecting plate 41 so as to cover the distal end of the heat exhausting portion 10, provide a protruding portion 42, which has a cross-sectional area that decreases continuously toward the distal end, on the top surface of the heat collecting plate 41, and form a plurality of inclined surfaces 43 that are inclined with respect to the bottom surfaces 14 of the plurality of piezoelectric elements 3.

Thus, by providing the heat collecting plate 41 so as to cover the distal end of the heat exhausting portion 10, heat can be efficiently conducted from the plurality of heat conducting paths 18 to the heat exhausting portion 10. In addition, since the plurality of inclined surfaces 43 are formed on the top surface of the heat collecting plate 41, the ultrasonic wave S emitted rearward from the plurality of piezoelectric elements 3 can be scattered by the inclined surfaces 43. Accordingly, since a situation is suppressed in which the ultrasonic wave S is reflected from the top surface of the heat collecting plate 41 or from the distal end of the heat exhausting portion 10 and is then incident on the bottom surfaces of the plurality of piezoelectric elements 3, it is possible to prevent noise or the like from being mixed in the received signal.

Preferably, the protruding portion 42 has a height of about $\lambda/10$ to several $\lambda$ so that the ultrasonic wave S from the plurality of piezoelectric elements 3 is effectively scattered. $\lambda$ is the wavelength of the ultrasonic wave S. Specifically, assuming that the frequency of the ultrasonic wave S is f=3.5 MHz and the material sound speed of the resin is v=2500 m/sec, the wavelength of the ultrasonic wave S propagating through the backing member 2 is λ=v/f=714 μm. For this reason, it is preferable that the height of the protruding portion 42 be about 0.1 mm to 3 mm.

In addition, the size of the protruding portion 42 may be non-uniform. In this case, it is preferable that the protruding portion 42 have an average height of λ/10 to several λ and an average base length of the same degree.

Fifth Embodiment

In the ultrasound probes of the first to fourth embodiments described above, cavities having a plurality of inclined surfaces that are inclined with respect to the bottom surfaces 14 of the plurality of piezoelectric elements 3 can be formed in the heat collecting plate 19.

Figure 7:
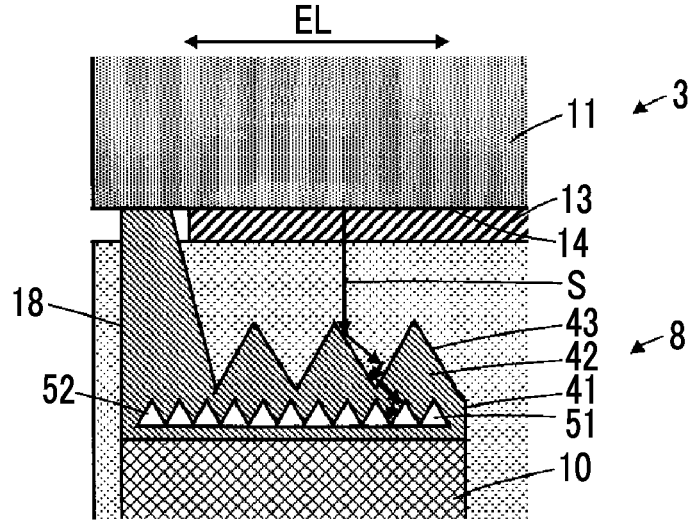
FIG. 7 is a cross-sectional view showing the configuration of an ultrasound probe according to a fifth embodiment.

For example, in the fourth embodiment, as shown in FIG. 7, it is possible to provide a plurality of cavities 51, which have a cross-sectional area that decreases continuously toward the distal end, in the heat collecting plate 41 and form a plurality of inclined surfaces 52 that are inclined with respect to the bottom surfaces 14 of the plurality of piezoelectric elements 3.

In this manner, the ultrasonic wave incident on the inside of the heat collecting portion 8 can be scattered downward by the plurality of inclined surfaces 52. For example, in the fourth embodiment, when the ultrasonic waves S emitted rearward from the plurality of piezoelectric elements 3 are scattered on the inclined surface 43, some of the ultrasonic waves S are incident on the inside of the heat collecting portion 8 through the inclined surface 43 as shown in FIG. 7. Therefore, compared with a case where the ultrasonic wave S incident on the inside of the heat collecting portion 8 is scattered again by the plurality of inclined surfaces 52, it is possible to further suppress a situation where the ultrasonic wave S is incident on the distal end of the heat exhausting portion 10 from the front. Thus, it is possible to more reliably suppress a situation where the ultrasonic wave S is reflected frontward by the distal end of the heat exhausting portion 10 and is then incident on the bottom surfaces of the plurality of piezoelectric elements 3.

Preferably, the cavity 51 has a height of about λ/10 to several λ so that the ultrasonic wave S incident on the inside of the heat collecting portion 8 is effectively scattered. λ is the wavelength of the ultrasonic wave S.

In addition, the size of the cavity 51 may be non-uniform. In this case, it is preferable that the cavity 51 have an average height of λ/10 to several λ and an average base length of the same degree.

The size of the cavity 51 may be appropriately designed in consideration of the relationship with the size of the protruding portion 42.

Sixth Embodiment

In the first to fifth embodiments described above, the plurality of heat conducting paths 18 are disposed only immediately below the pair of edge portions 15a and 15b on the bottom surfaces 14 of the plurality of piezoelectric elements 3. However, the plurality of heat conducting paths 18 can also be disposed immediately below the intermediate portions 16 of a plurality of piezoelectric elements 3.

Figure 8:
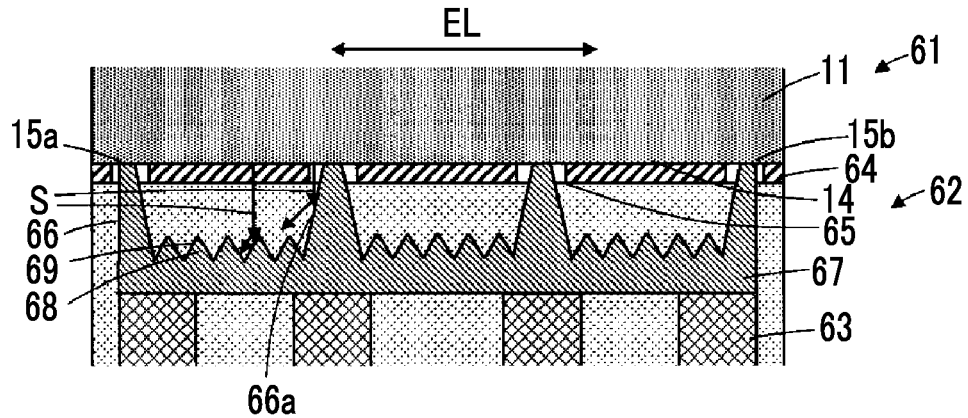
FIG. 8 is a cross-sectional view showing the configuration of an ultrasound probe according to a sixth embodiment.

For example, in the ultrasound probe according to the first embodiment, as shown in FIG. 8, a plurality of piezoelectric elements 61, a heat collecting portion 62, and a heat exhausting portion 63 can be disposed instead of the plurality of piezoelectric elements 3, the heat collecting portion 8, and the heat exhausting portion 10.

In the plurality of piezoelectric elements 61, a signal electrode layer 64 that covers the entire bottom surface 14 of each piezoelectric body 11 is disposed instead of the signal electrode layer 13 of the first embodiment. In each signal electrode layer 64, a plurality of openings 65 are formed at positions corresponding to the pair of edge portions 15a and 15b and the intermediate portion 16 of the piezoelectric body 11 so as to be arrayed in the elevation direction EL.

The heat collecting portion 62 includes a plurality of heat conducting paths 66 and a heat collecting plate 67. The plurality of heat conducting paths 66 are arrayed in the elevation direction EL immediately below the pair of edge portions 15a and 15b and immediately below the intermediate portion 16 in each piezoelectric body 11. The distal ends of the plurality of heat conducting paths 66 are in direct contact with the pair of edge portions 15a and 15b and the intermediate portion 16 of the piezoelectric body 11 through the plurality of openings 65 formed in the signal electrode layer 64. In addition, similar to the plurality of heat conducting paths 18 in the first embodiment, the plurality of heat conducting paths 66 are arrayed in a row in the azimuth direction AZ so as to correspond to the piezoelectric elements 61.

Thus, by increasing the number of heat conducting paths 66 in contact with the bottom surfaces 14 of the plurality of piezoelectric elements 61, heat generated in the plurality of piezoelectric elements 61 can be more efficiently transferred to the plurality of heat conducting paths 66. As a result, it is possible to reliably suppress the temperature rise of the plurality of piezoelectric elements 61.

In addition, it is preferable that the plurality of heat conducting paths 66 be arrayed at fixed distances therebetween in the elevation direction. In this case, since the heat generated in the plurality of piezoelectric elements 61 can be transferred to the plurality of heat conducting paths 66 almost uniformly from the bottom surface 14, it is possible to more reliably suppress the temperature rise of the plurality of piezoelectric elements 61.

The heat collecting plate 67 has a shape that extends continuously in the elevation direction EL so that the base ends of all of the heat conducting paths 66 are connected. That is, the heat collecting plate 67 is disposed so as to extend continuously from the position of the heat conducting path 66 bonded to one edge portion 15a of the piezoelectric body 11 to the position of the heat conducting path 66 bonded to the other edge portion 15b. By connecting the base ends of all of the heat conducting paths 66 as described above, heat conducted through the plurality of heat conducting paths 66 can be efficiently collected into the heat collecting plate 67.

The heat exhausting portion 63 is connected to the bottom surface of the heat collecting plate 67 so as to correspond to the plurality of heat conducting paths 66. Therefore, the heat collected in the heat collecting plate 67 can be efficiently discharged to the outside.

In addition, each of the plurality of heat conducting paths 66 is formed such that the cross-sectional area is continuously decreased toward the distal end, and has an inclined surface 66a, which is inclined with respect to the bottom surfaces 14 of the plurality of piezoelectric elements 61, as its top surface. Due to the inclined surface 66a, the ultrasonic wave S emitted rearward from the plurality of piezoelectric elements 61 can be scattered.

In addition, a protruding portion 68 having a cross-sectional area that decreases continuously toward the distal end is formed on the top surface of the heat collecting plate 67, and a plurality of inclined surfaces 69 that are inclined with respect to the bottom surfaces 14 of the plurality of piezoelectric elements 61 are formed on the protruding portion 68. Due to the inclined surface 69, the ultrasonic wave S emitted rearward from the plurality of piezoelectric elements 61 can be scattered more effectively. In addition, similar to the protruding portion 42 in the fourth embodiment, it is preferable that the protruding portion 68 have a height of about λ/10 to several λ so that the ultrasonic wave S from the plurality of piezoelectric elements 3 is reliably scattered. λ is the wavelength of the ultrasonic wave S. In addition, the size of the protruding portion 68 may be non-uniform. In this case, it is preferable that the protruding portion 68 have an average height of λ/10 to several λ and an average base length of the same degree.

According to the present embodiment, due to the inclined surfaces 66a and 69 formed across the entire top surface facing the bottom surfaces 14 of the plurality of piezoelectric elements 61, it is possible to reliably suppress a situation where the ultrasonic wave S emitted rearward from the plurality of piezoelectric elements 61 is reflected frontward and is then incident on the bottom surfaces 14 of the plurality of piezoelectric elements 61 while the heat generated in the plurality of piezoelectric elements 61 can be more efficiently discharged to the outside by making a larger number of heat conducting paths 66 in contact with the bottom surfaces 14 of the plurality of piezoelectric elements 61.

Seventh Embodiment

In the first to sixth embodiments described above, the distal ends of the plurality of heat conducting paths are in direct contact with the bottom surfaces 14 of the piezoelectric bodies in the plurality of piezoelectric elements. However, the distal ends of the plurality of heat conducting paths can also be in direct contact with the bottom surface of the signal electrode layer.

Figure 9:
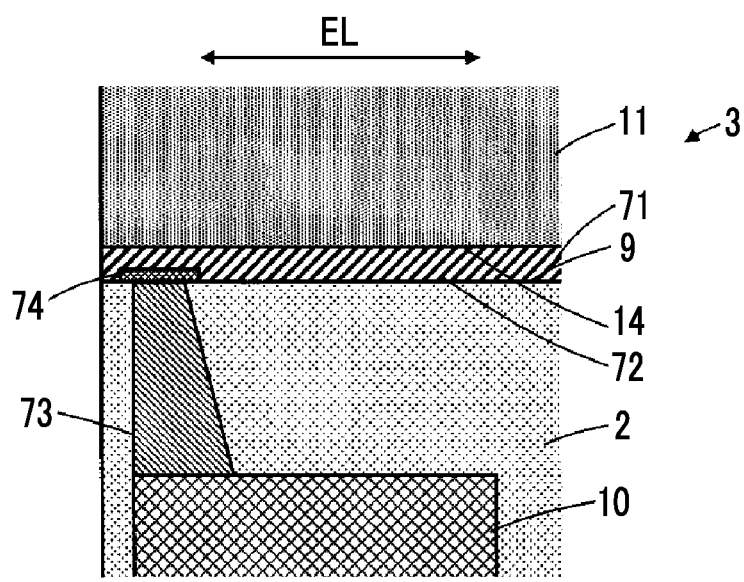
FIG. 9 is a cross-sectional view showing the configuration of an ultrasound probe according to a seventh embodiment.

For example, as shown in FIG. 9, in the ultrasound probe according to the first embodiment, a signal electrode layer 71 can be disposed across the entire bottom surface 14 of the piezoelectric body 11 instead of the signal electrode layer 13, and the bottom surface 72 of the signal electrode layer 71 can be made to be in contact with the distal ends of the plurality of heat conducting paths 73 exposed from the top surface 9 of the backing member 2 with an insulating layer 74 interposed therebetween.

Therefore, the heat generated in the plurality of piezoelectric elements 3 can be conducted from the bottom surface 72 of the signal electrode layer 71 to the plurality of heat conducting paths 73 through the insulating layer 74.

According to the present embodiment, since it is not necessary to bring a plurality of heat conducting paths into contact with the piezoelectric body by aligning the plurality of heat conducting paths so as not to be in contact with the signal electrode layer, it is possible to easily bring the plurality of heat conducting paths 73 into contact with the bottom surfaces 72 of the plurality of piezoelectric elements 3.

Eighth Embodiment

In the first to seventh embodiments described above, in the plurality of piezoelectric elements, the ground electrode layer is bonded to the top surface of the piezoelectric body, and the signal electrode layer is bonded to the bottom surface of the piezoelectric body. However, the signal electrode layer may be bonded to the top surface of the piezoelectric body, and the ground electrode layer may be bonded to the bottom surface of the piezoelectric body.

Figure 10:
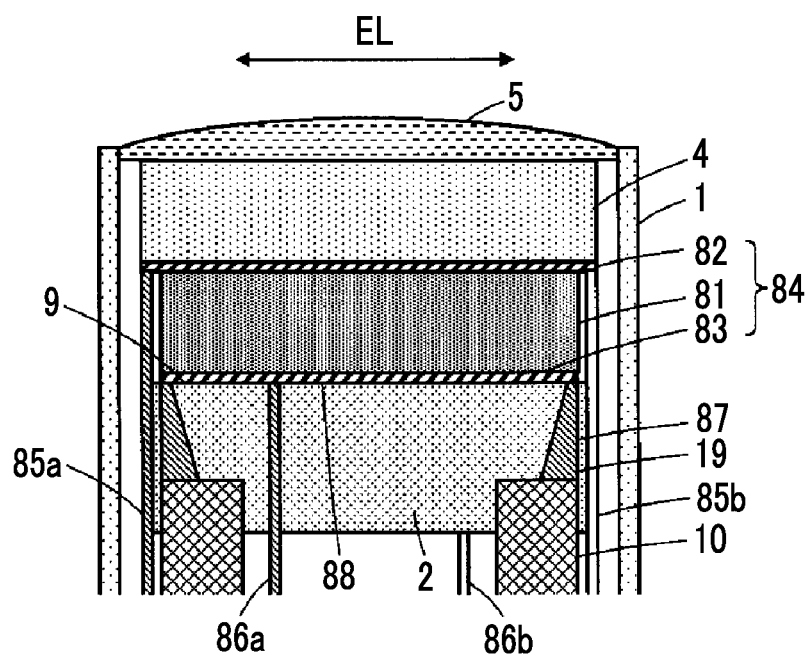
FIG. 10 is a cross-sectional view showing the configuration of an ultrasound probe according to an eighth embodiment.

For example, as shown in FIG. 10, in the ultrasound probe according to the first embodiment, a plurality of piezoelectric elements 84 in which a signal electrode layer 82 is bonded to the top surface of each piezoelectric body 81 and a ground electrode layer 83 is bonded to the bottom surface of each piezoelectric body 81 can be disposed instead of the plurality of piezoelectric elements 3. The ground electrode layer 83 is disposed so as to cover the entire bottom surface of the piezoelectric body 81.

In addition, signal lines 85a and 85b are disposed instead of the ground lines 6a and 6b in the first embodiment, and ground lines 86a and 86b are disposed instead of the signal lines 7a and 7b in the first embodiment. The signal lines 85a and 85b are connected to the signal electrode layer 82, and the ground lines 86a and 86b are connected to the ground electrode layer 83.

In addition, a plurality of heat conducting paths 87 having distal ends exposed from the top surface 9 of the backing member 2 are disposed instead of the plurality of heat conducting paths 18 in the first embodiment. The distal ends of the plurality of heat conducting paths 87 are in direct contact with a bottom surface 88 of the ground electrode layer 83.

Thus, by arranging the ground electrode layer 83 on the bottom surface side of the piezoelectric body 81, the distal ends of the plurality of heat conducting paths 87 can be brought into direct contact with the bottom surface 88 of the ground electrode layer 83 without providing an insulating layer or the like shown in the seventh embodiment.

According to the present embodiment, since it is not necessary to bring a plurality of heat conducting paths into contact with the piezoelectric body by aligning the plurality of heat conducting paths so as not to be in contact with the signal electrode layer, it is possible to easily bring the plurality of heat conducting paths 87 into contact with the bottom surfaces 88 of the plurality of piezoelectric elements 84.

Ninth Embodiment

In the first to eighth embodiments described above, a plurality of piezoelectric elements are bonded onto the surface of the backing member. However, a de-matching layer for reflecting the ultrasonic wave, which is emitted rearward from the plurality of piezoelectric elements, to the front can be disposed between the backing member and the plurality of piezoelectric elements.

Figure 11:
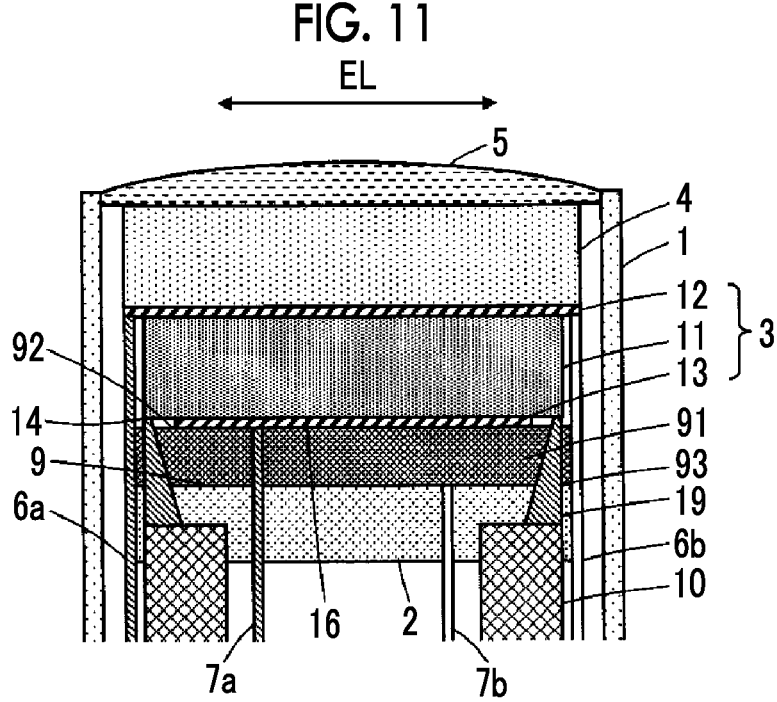
FIG. 11 is a cross-sectional view showing the configuration of an ultrasound probe according to a ninth embodiment.

For example, as shown in FIG. 11, in the ultrasound probe according to the first embodiment, a de-matching layer 91 can be disposed between the backing member 2 and the plurality of piezoelectric elements 3. Here, it is assumed that the de-matching layer 91 has a larger acoustic impedance than the piezoelectric body 11 of each of the plurality of piezoelectric elements 3.

In addition, a plurality of heat conducting paths 93 extending from the inside of the backing member 2 to the inside of the de-matching layer 91 can be disposed instead of the plurality of heat conducting paths 18 in the first embodiment. The distal ends of the plurality of heat conducting paths 93 are exposed from the top surface 92 of the de-matching layer 91 and extend toward the bottom surface 14 of the piezoelectric body 11 to be in direct contact with the bottom surface 14.

Thus, in the ultrasound probes according to the first to eighth embodiments, it is possible to dispose a de-matching layer between the backing member and the plurality of piezoelectric elements.

According to the present embodiment, also in the ultrasound probe in which the de-matching layer 91 is disposed, heat generated in the plurality of piezoelectric elements 3 can be efficiently discharged to the outside. Therefore, it is possible to increase the driving force of the plurality of piezoelectric elements 3 while maintaining the low surface temperature of the acoustic lens 5.

Tenth Embodiment

In the first to ninth embodiments described above, it is preferable that the base end of the heat exhausting portion be connected to a metal portion provided in the housing.

Figure 12:
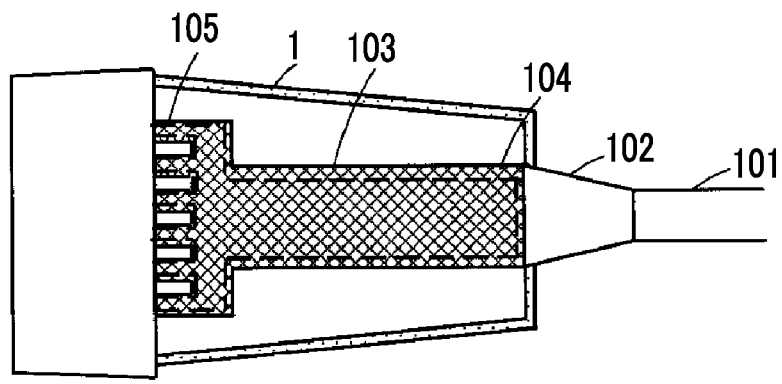
FIG. 12 is a cross-sectional view showing the configuration of an ultrasound probe according to a tenth embodiment.

For example, as shown in FIG. 12, a connection cable 101 for connecting ground lines and signal lines connected to a plurality of piezoelectric elements to the main body of an ultrasound diagnostic apparatus (not shown) can be connected to the base end of the housing 1 through a connecting portion 102 formed of a metal, and a base end 104 of a heat exhausting portion 103 can be connected to the connecting portion 102. The heat exhausting portion 103 is connected to a heat collecting portion, and has a plurality of distal ends 105 extending in parallel to each other corresponding to the plurality of piezoelectric elements and a base end 104 for integrating the plurality of distal ends 105 to one heat pipe.

According to the present embodiment, it is possible to promote the cooling of the base end 104 by connecting the base end 104 of the heat exhausting portion 103 to the metal portion of the housing 1. Therefore, the heat collected in the heat collecting portion can be efficiently discharged to the outside.

Figure 13:
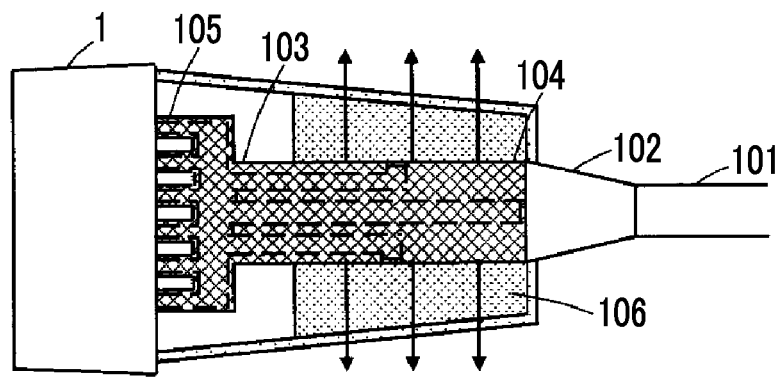
FIG. 13 is a cross-sectional view showing the configuration of an ultrasound probe according to a modification example of the tenth embodiment.

In addition, as shown in FIG. 13, it is preferable to dispose a heat exhausting member 106 so as to fill the space between the outer peripheral wall of the heat exhausting portion 103 and the inner wall of the housing 1. The heat exhausting member 106 is preferably formed of a material having a high thermal conductivity. In this case, for example, the base end 104 of the heat exhausting portion 103 can integrate the plurality of distal ends 105 to three heat pipes. The base end of one heat pipe can be connected to the connecting portion 102, and the base ends of two heat pipes can be connected to the heat exhausting member 106.

Therefore, since the heat transferred to the base end 104 of the heat exhausting portion 103 is also discharged from the side wall of the housing 1 through the heat exhausting member 106, the heat collected in the heat collecting portion 8 can be more efficiently discharged to the outside.

The heat exhausting member 106 can be formed of composite resin obtained by mixing a resin material with metal particles, for example.

In addition, in the first to tenth embodiments described above, the distal ends of the plurality of heat conducting paths are in direct contact with a pair of edge portions extending in the azimuth direction AZ on the bottom surfaces of the plurality of piezoelectric elements. However, the plurality of heat conducting paths can be disposed immediately below at least one of the pair of edge portions of the plurality of piezoelectric elements, and the distal ends can be in direct contact with at least one of the pair of edge portions of the plurality of piezoelectric elements.

In addition, although the plurality of heat conducting paths are formed so as to have a cross-sectional area that decreases continuously toward the distal ends in the first to tenth embodiments described above, the plurality of heat conducting paths can also be formed so as to have a cross-sectional area that decreases stepwise toward the distal ends.

Figure 14:
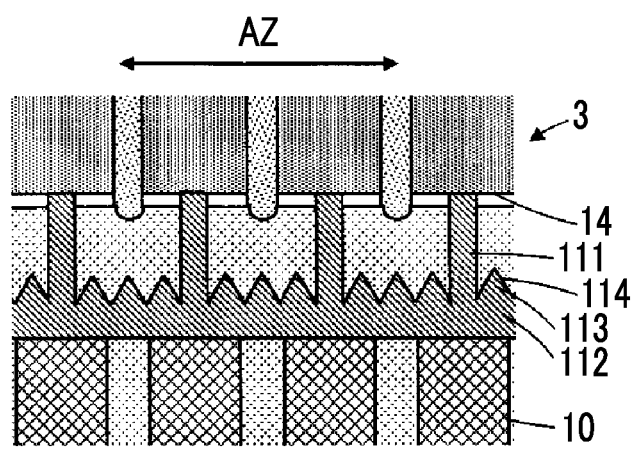
FIG. 14 is a cross-sectional view showing a plurality of heat conducting paths according to the modification example.

As shown in FIG. 14, it is also possible to form a plurality of heat conducting paths 111 so as to extend linearly toward the bottom surfaces 14 of the plurality of piezoelectric elements 3. In this case, it is preferable to provide a protruding portion 113, which has a cross-sectional area that decreases continuously toward the distal end, on the top surface of the heat collecting plate 112 connecting the plurality of heat conducting paths 111 to each other and to form a plurality of inclined surfaces 114 that are inclined with respect to the bottom surfaces 14 of the plurality of piezoelectric elements 3. In addition, similar to the protruding portion 42 in the fourth embodiment, it is preferable that the protruding portion 113 have a height of about $\lambda/10$ to several $\lambda$ so that the ultrasonic wave S from the plurality of piezoelectric elements 3 is reliably scattered. $\lambda$ is the wavelength of the ultrasonic wave S. In addition, the size of the protruding portion 113 may be non-uniform. In this case, it is preferable that the protruding portion 113 have an average height of $\lambda/10$ to several $\lambda$ and an average base length of the same degree.

Figure 15:
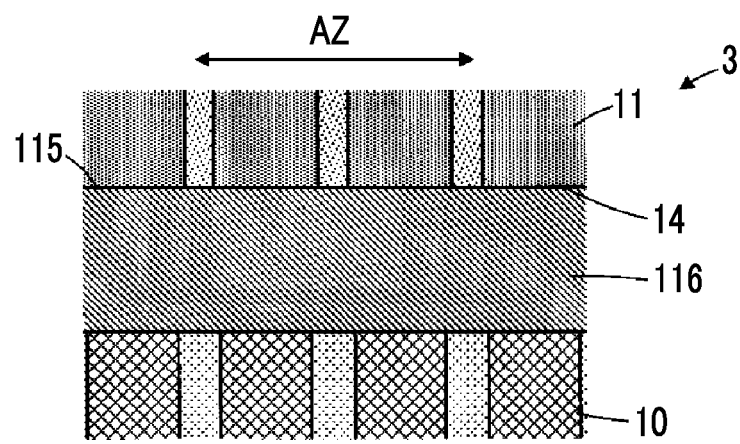
FIG. 15 is a cross-sectional view showing a plurality of heat conducting paths according to another modification example.

In addition, as shown in FIG. 15, it is also possible to provide a heat conducting path 116 that has a flat plate shape and that has a distal end 115 that is continuously connected to the bottom surfaces 14 of the plurality of piezoelectric elements 3. The flat plate shape extends toward the bottom surfaces 14 of the plurality of piezoelectric elements 3 from the heat exhausting portion 10 and extends in the azimuth direction AZ across all of the piezoelectric elements 3. The heat conducting path 116 is disposed immediately below at least one of the pair of edge portions of the plurality of piezoelectric elements 3, and the distal end 115 is in direct contact with at least one of the pair of edge portions of the plurality of piezoelectric elements 3. That is, at least one heat conducting path 116 is disposed immediately below the pair of edge portions of the plurality of piezoelectric elements 3, and the distal end is in direct contact with a pair of edge portions. Thus, the heat conducting path 116 is in contact with a pair of edge portions of the piezoelectric body 11 that expand and contract little. Therefore, the expansion and contraction of the piezoelectric body 11 are not significantly inhibited.

In addition, although the heat exhausting portion is formed by heat pipes in the first to tenth embodiments described above, the heat exhausting portion is not limited to the heat pipe as long as the heat exhausting portion can have a thermal conductivity equal to or higher than the heat collecting portion.

In addition, although a plurality of piezoelectric elements are arrayed in a row in the elevation direction EL in the first to tenth embodiments described above, a plurality of piezoelectric elements can also be arrayed in a two-dimensional manner in the elevation direction EL and the azimuth direction AZ. In this case, it is preferable to bring the distal ends of the plurality of heat conducting paths into direct contact with the bottom surfaces of the respective piezoelectric elements.

In addition, the ultrasound probes according to the first to tenth embodiments described above can also be applied to an ultrasonic endoscope.

What is claimed is:
1. An ultrasound probe, comprising:
a backing member;

a plurality of piezoelectric elements arrayed on a top surface of the backing member;
a heat collecting portion that includes at least one heat conducting path, is formed of a material having a higher thermal conductivity than the backing member, and collects heat from the plurality of piezoelectric elements, the heat conducting path extending in a thickness direction within the backing member and having a distal end exposed from the top surface of the backing member facing a bottom surface of each of the plurality of piezoelectric elements; and
a heat exhausting portion that is connected to the heat collecting portion and discharges heat collected in the heat collecting portion to an outside,
wherein the heat conducting path is disposed immediately below at least one of a pair of edge portions extending in an azimuth direction on the bottom surface of each of the plurality of piezoelectric elements, and the distal end is in direct contact with at least one of the pair of edge portions of each of the plurality of piezoelectric elements.

2. The ultrasound probe according to claim 1, wherein the heat conducting path is disposed immediately below an intermediate portion located between the pair of edge portions on the bottom surface of each of the plurality of piezoelectric elements, and the distal end is in direct contact with the intermediate portion of each of the plurality of piezoelectric elements.

3. The ultrasound probe according to claim 2, further comprising:
a plurality of separating portions that are filled between the plurality of piezoelectric elements in order to separate the plurality of piezoelectric elements from each other and that are formed of a material having a higher thermal conductivity than the backing member,
wherein the heat conducting path is disposed immediately below the plurality of separating portions, and the distal end is in direct contact with the plurality of separating portions.

4. The ultrasound probe according to claim 3, further comprising:
a de-matching layer disposed between the backing member and the plurality of piezoelectric elements,
wherein the heat conducting path extends from an inside of the backing member to an inside of the de-matching layer, and the distal end is exposed from a top surface of the de-matching layer.

5. The ultrasound probe according to claim 2, further comprising:
a de-matching layer disposed between the backing member and the plurality of piezoelectric elements,
wherein the heat conducting path extends from an inside of the backing member to an inside of the de-matching layer, and the distal end is exposed from a top surface of the de-matching layer.

6. The ultrasound probe according to claim 2, wherein the heat conducting path has a shape having a cross-sectional area that decreases toward the distal end.

7. The ultrasound probe according to claim 1, further comprising:
a plurality of separating portions that are filled between the plurality of piezoelectric elements in order to separate the plurality of piezoelectric elements from each other and that are formed of a material having a higher thermal conductivity than the backing member,
wherein the heat conducting path is disposed immediately below the plurality of separating portions, and the distal end is in direct contact with the plurality of separating portions.

8. The ultrasound probe according to claim 1, further comprising:
a plurality of separating portions that are filled between the plurality of piezoelectric elements in order to separate the plurality of piezoelectric elements from each other and that are formed of a material having a higher thermal conductivity than the backing member,
wherein the heat conducting path is disposed immediately below the plurality of separating portions, and the distal end is in direct contact with the plurality of separating portions.

9. The ultrasound probe according to claim 8, further comprising:
a de-matching layer disposed between the backing member and the plurality of piezoelectric elements,
wherein the heat conducting path extends from an inside of the backing member to an inside of the de-matching layer, and the distal end is exposed from a top surface of the de-matching layer.

10. The ultrasound probe according to claim 1, further comprising:
a de-matching layer disposed between the backing member and the plurality of piezoelectric elements,
wherein the heat conducting path extends from an inside of the backing member to an inside of the de-matching layer, and the distal end is exposed from a top surface of the de-matching layer.

11. The ultrasound probe according to claim 1, wherein the heat conducting path has a shape having a cross-sectional area that decreases toward the distal end.

12. The ultrasound probe according to claim 1, wherein the heat collecting portion includes a heat collecting plate connected to a base end of the heat conducting path.

13. The ultrasound probe according to claim 1, wherein the heat exhausting portion is a heat pipe having a distal end connected to the heat collecting portion.

14. An ultrasound probe, comprising:
a backing member;
a plurality of piezoelectric elements arrayed on a top surface of the backing member;
a heat collecting portion that includes at least one heat conducting path, is formed of a material having a higher thermal conductivity than the backing member, and collects heat from the plurality of piezoelectric elements, the heat conducting path extending in a thickness direction within the backing member and having a distal end exposed from the top surface of the backing member facing a bottom surface of each of the plurality of piezoelectric elements;
a heat exhausting portion that is connected to the heat collecting portion and discharges heat collected in the heat collecting portion to an outside; and
a de-matching layer disposed between the backing member and the plurality of piezoelectric elements,
wherein the heat conducting path extends from an inside of the backing member to an inside of the de-matching layer, and the distal end is exposed from a top surface of the de-matching layer.

15. An ultrasound probe, comprising:
a backing member;

a plurality of piezoelectric elements arrayed on a top surface of the backing member;
a heat collecting portion that includes at least one heat conducting path, is formed of a material having a higher thermal conductivity than the backing member, and collects heat from the plurality of piezoelectric elements, the heat conducting path extending in a thickness direction within the backing member and having a distal end exposed from the top surface of the backing member facing a bottom surface of each of the plurality of piezoelectric elements;
a heat exhausting portion that is connected to the heat collecting portion and discharges heat collected in the heat collecting portion to an outside;
a de-matching layer disposed between the backing member and the plurality of piezoelectric elements; and
a plurality of separating portions that are filled between the plurality of piezoelectric elements in order to separate the plurality of piezoelectric elements from each other and that are formed of a material having a higher thermal conductivity than the backing member,
wherein the heat conducting path extends from an inside of the backing member to an inside of the de-matching layer, and the distal end is exposed from a top surface of the de-matching layer, and
wherein the heat conducting path is disposed immediately below the plurality of separating portions, and the distal end is in direct contact with the plurality of separating portions.

16. An ultrasound probe, comprising:
a backing member;
a plurality of piezoelectric elements arrayed on a top surface of the backing member;
a heat collecting portion that includes at least one heat conducting path, is formed of a material having a higher thermal conductivity than the backing member, and collects heat from the plurality of piezoelectric elements, the heat conducting path extending in a thickness direction within the backing member and having a distal end exposed from the top surface of the backing member facing a bottom surface of each of the plurality of piezoelectric elements; and
a heat exhausting portion that is connected to the heat collecting portion and discharges heat collected in the heat collecting portion to an outside,
wherein the heat collecting plate is disposed inside the backing member and has a plurality of inclined surfaces on a surface facing the plurality of piezoelectric elements, the inclined surfaces being inclined with respect to the bottom surfaces of the plurality of piezoelectric elements, and
wherein the heat collecting portion includes a heat collecting plate connected to a base end of the heat conducting path.

17. The ultrasound probe according to claim 16,
wherein the heat collecting plate is disposed inside the backing member and includes cavities, and the cavities have a plurality of inclined surfaces that are inclined with respect to the bottom surfaces of the plurality of piezoelectric elements.

18. An ultrasound probe, comprising:
a backing member;
a plurality of piezoelectric elements arrayed on a top surface of the backing member;
a heat collecting portion that includes at least one heat conducting path, is formed of a material having a higher thermal conductivity than the backing member, and collects heat from the plurality of piezoelectric elements, the heat conducting path extending in a thickness direction within the backing member and having a distal end exposed from the top surface of the backing member facing a bottom surface of each of the plurality of piezoelectric elements; and
a heat exhausting portion that is connected to the heat collecting portion and discharges heat collected in the heat collecting portion to an outside,
wherein the heat collecting plate is disposed inside the backing member and includes cavities, and the cavities have a plurality of inclined surfaces that are inclined with respect to the bottom surfaces of the plurality of piezoelectric elements, and
wherein the heat collecting portion includes a heat collecting plate connected to a base end of the heat conducting path.

* * * * *